(12) United States Patent
Chiang et al.

(10) Patent No.: US 12,186,240 B2
(45) Date of Patent: Jan. 7, 2025

(54) CONVERTIBLY PREFABRICATED MODULAR INPATIENT UNIT WITH ENABLING CONTINUOUS RECONFIGURATION AND REDEPLOYMENT

(71) Applicant: Fu Jen Catholic University Hospital, Fu Jen Catholic University, New Taipei (TW)

(72) Inventors: Han-Sun Chiang, New Taipei (TW); Ching-Chuan Jiang, New Taipei (TW); Heng-Tai Chao, New Taipei (TW); Wei-Lun Liu, New Taipei (TW); Yi-Jen Jiang, New Taipei (TW); Shiau-Jiun Lai, New Taipei (TW); Heng-Lang Lin, New Taipei (TW); Po-Jui Yu, New Taipei (TW); Chin-Yu Hsieh, New Taipei (TW); Chia-Jung Tsai, New Taipei (TW); Yu-Hsuan Wu, New Taipei (TW)

(73) Assignee: FU JEN CATHOLIC UNIVERSITY HOSPITAL, FU JEN CATHOLIC UNIVERSITY, New Taipei (TW)

( * ) Notice: Subject to any disclaimer, the term of this patent is extended or adjusted under 35 U.S.C. 154(b) by 931 days.

(21) Appl. No.: 17/237,555

(22) Filed: Apr. 22, 2021

(65) Prior Publication Data
US 2021/0330533 A1    Oct. 28, 2021

Related U.S. Application Data

(60) Provisional application No. 63/013,822, filed on Apr. 22, 2020.

(51) Int. Cl.
| | |
|---|---|
| A61G 10/00 | (2006.01) |
| A61G 10/02 | (2006.01) |
| A61L 9/20 | (2006.01) |
| E04H 1/00 | (2006.01) |
| E04H 1/12 | (2006.01) |

(52) U.S. Cl.
CPC ........... *A61G 10/005* (2013.01); *A61G 10/02* (2013.01); *A61L 9/205* (2013.01); *E04H 1/005* (2013.01); *E04H 1/12* (2013.01); *A61L 2209/14* (2013.01); *A61L 2209/16* (2013.01)

(58) Field of Classification Search
CPC .... A61M 21/0094; A62B 29/00; A62B 31/00; A61B 90/05; A61B 90/40; A61B 2090/401
See application file for complete search history.

(56) References Cited

U.S. PATENT DOCUMENTS

| | | | | |
|---|---|---|---|---|
| 5,152,814 | A * | 10/1992 | Nelson | F24F 3/167 55/385.2 |
| 2002/0104271 | A1* | 8/2002 | Gallant | E04B 2/7448 52/270 |

(Continued)

*Primary Examiner* — Thaddeus B Cox
(74) *Attorney, Agent, or Firm* — MUNCY, GEISSLER, OLDS & LOWE, P.C.

(57) ABSTRACT

The present invention provides an inpatient unit of modular design, built of recycled materials and environmentally friendly materials, allowing reconfiguration, redeployment and quick assembly, preventing indoor air from leaking, applicable to epidemic prevention and treating special patients, with high structural strength, lower cost and good environmental benefit.

7 Claims, 11 Drawing Sheets

(56) References Cited

U.S. PATENT DOCUMENTS

| | | | | |
|---|---|---|---|---|
| 2008/0041399 | A1* | 2/2008 | Kriek | A61B 90/40 |
| | | | | 128/853 |
| 2013/0000561 | A1* | 1/2013 | Park | A63B 23/18 |
| | | | | 119/420 |
| 2017/0333267 | A1* | 11/2017 | Anandasabapathy | E04H 3/08 |
| 2018/0110666 | A1* | 4/2018 | Yim | E04H 3/08 |
| 2021/0015959 | A1* | 1/2021 | Goseki | A61L 9/20 |

* cited by examiner

CONVERTIBLY PREFABRICATED MODULAR INPATIENT UNIT WITH ENABLING CONTINUOUS RECONFIGURATION AND REDEPLOYMENT

BACKGROUND OF INVENTION

1. Field of the Invention

The present invention relates generally to a prefabricated modular inpatient unit with environmentally friendly materials which allows reconfiguration, redeployment and quick assembly, prevents indoor air from leaking and can be used for epidemic prevention.

2. Description of Related Art

Since the 20th century, emerging infectious diseases have not been occasional incidents in human history. The spread of these infectious diseases is mainly resulted from good traffic network, e.g. air traffic, global travel or business negotiation, the diseases can get to the destination within a day. In other words, as the number of migrants and tourists increases rapidly, once an emerging infectious disease spreads in the crowds, and the infected individuals are nonimmune to the pathogen of the infectious disease, the spread velocity of infectious disease increases accordingly.

Many symptoms of the patients with the emerging infectious diseases, such as the acute respiratory disease, are nonspecific, and the medical units usually lack rapid diagnosis, and often fail to find the cause of disease. For example, the acute respiratory disease, namely the pandemic coronavirus disease 2019 (COVID19) induced by severe acute respiratory syndrome coronavirus 2 (SARSCoV-2), was announced by the World Health Organization (WHO) on Mar. 1, 2020.

According to epidemiological investigation and laboratory testing of confirmed cases, close droplets, directly or indirectly contacting the oral and nasal secretion with virus, or staying within 2 meter from the confirmed patients in a confined space without respiratory protection for a long time will increase the interpersonal infection risk. To avoid massive outbreak of infectious diseases, and to minimize the probability of infecting the medical care personnel themselves, the other medical care personnel, patients and visitors, the importance of adopting infection prevention and control measures in the medical environment cannot be underrated.

In other words, in the aforesaid medical unit for treating the patients with acute respiratory disease, the viruses or bacteria in the ward may enter another ward through the flow of persons and air flow, that is likely to cause cross infection. Therefore, it is important and urgent to provide wards which are unlikely to leak indoor air and to exchange air with the outside. For example, the negative pressure isolation room has special devices for air-conditioning system and air input/output, the room only admits air, not discharges air. The medical unit shall use this kind of negative pressure isolation room to isolate COVID19 patients, so as to prevent the epidemic situation from spreading.

However, it is difficult to collect related equipments, materials and manpower to organize a lot of negative pressure isolation rooms for the region with serious epidemic situation in a short period of time. Moreover, most of the temporary wards built by using the existing technology are formed integrally, large sized and difficult for transportation, and the assembly takes a long time. Furthermore, the disposal after use of the temporary wards built by using the existing technology is relatively complex. Therefore, a prefabricated modular inpatient unit with a negative pressure isolation space made of recycled materials and environmentally friendly materials which can be assembled quickly and used in any field domain is an urgent demand.

SUMMARY OF THE INVENTION

As stated above, how to provide an inpatient unit built of recycled materials and environmentally friendly materials by modular design, which allows reconfiguration, redeployment and quick assembly, prevents indoor air from leaking to the outside, and can be used for epidemic prevention, and is modular, adaptable and convertible. The prefabricated modular inpatient unit of the present invention can be used to assemble different kinds of wards quickly in any place, e.g. intensive care unit, general ward, isolation room or negative pressure ward. It can be used as general ward in outdoor environment, e.g. parking lot, stadium and gymnasium, and it is convertible according to application requirement. That is an urgent issue for public health units and medical units.

The present invention provides a convertibly prefabricated modular inpatient unit with enabling continuous reconfiguration and redeployment, comprising a main body of inpatient unit, the main body of inpatient unit comprises two long walls, two short walls, an inner ceiling and a PVC seamless floor.

In an embodiment of the present invention, two long walls and two short walls are arranged oppositely on both sides of the main body of inpatient unit respectively.

In an embodiment of the present invention, the long walls and the short walls are assembled of a plurality of inner unit panels and a plurality of outer unit panels, a plurality of outer unit panels assemble the outer wall, the adjacent inner unit panels are fixed by a plurality of panel connecting pieces, the joints of the adjacent inner unit panels towards the inner space of modular inpatient unit are tightened by a plurality of antibacterial airtight pieces, the antibacterial airtight pieces are made of a polyolefins TPV, the inner unit panels and outer unit panels are made of recycled PET, and the inner unit panels are spray coated with aluminum nano-photocatalyst material.

In an embodiment of the present invention, the joint of the inner ceiling and the inner wall towards the inner space of modular inpatient unit forms a top circular arc chamfer, the inner ceiling towards the inner space of modular inpatient unit is assembled of a plurality of polycarbonate recycled plastic hollow panels, the adjacent polycarbonate recycled plastic hollow panels are fixed by a plurality of top panel connecting pieces.

In an embodiment of the present invention, the PVC seamless floor is arranged opposite the inner ceiling under the inner wall, the PVC seamless floor is formed by laying a PVC sheet, the joint of the PVC seamless floor and one of the long walls or the short walls towards the inner space of the modular inpatient unit forms a seamless bottom circular arc chamfer.

In an embodiment of the present invention, the inner ceiling is provided with at least one fresh air outlet, an independent air conditioning cold setting unit, wherein one of the long walls provided with a return air inlet is adjacent to one sickbed, wherein the return air inlet is provided with a HEPA for treatment of exhaust air, wherein the fresh air outlet, the return air inlet and the independent air conditioning cold setting unit assemble a negative pressure air conditioning system.

To make the aforesaid features and advantages of the present invention more intelligible, there are embodiments given below, and elaborated with attached figures as follows.

DETAILED DESCRIPTION OF THE INVENTION

Figure 1:
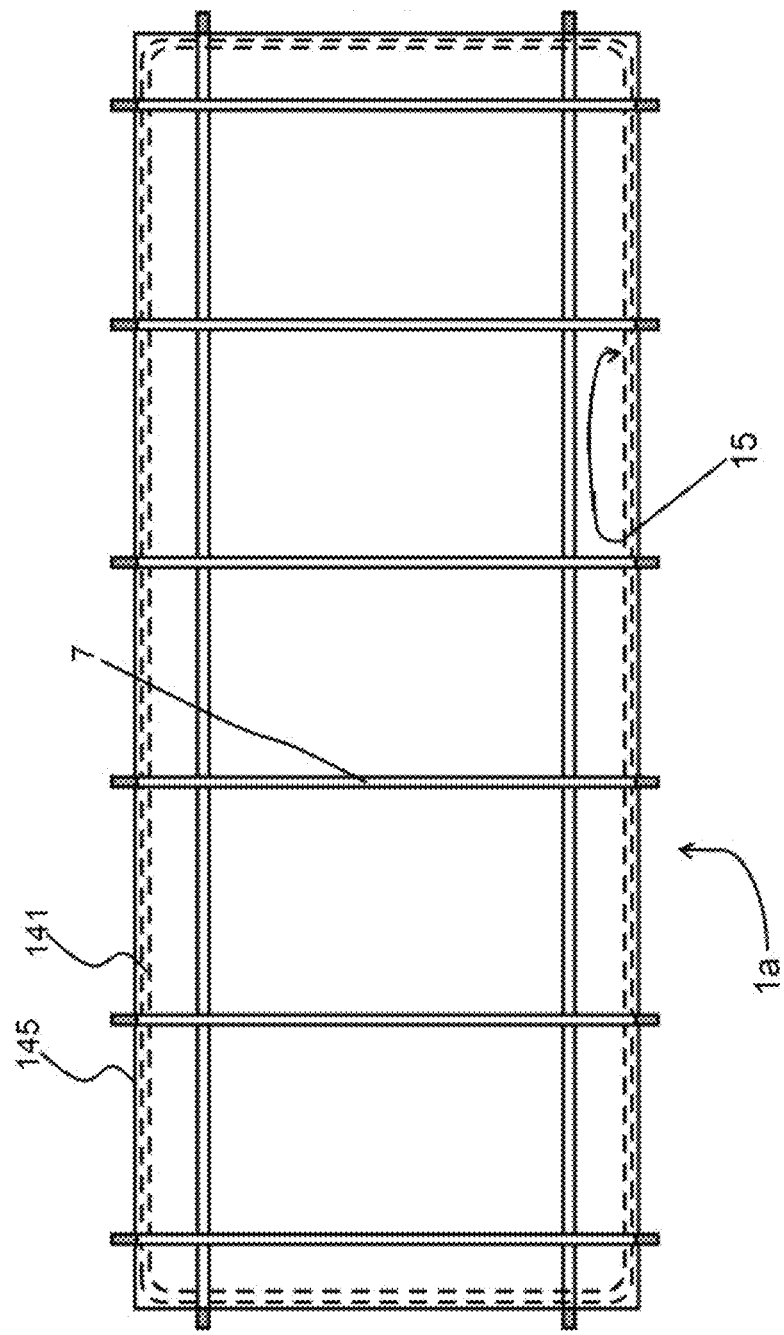
FIG. 1 is the schematic cross section of a main body of inpatient unit in one embodiment of the present invention.
Figure 2:
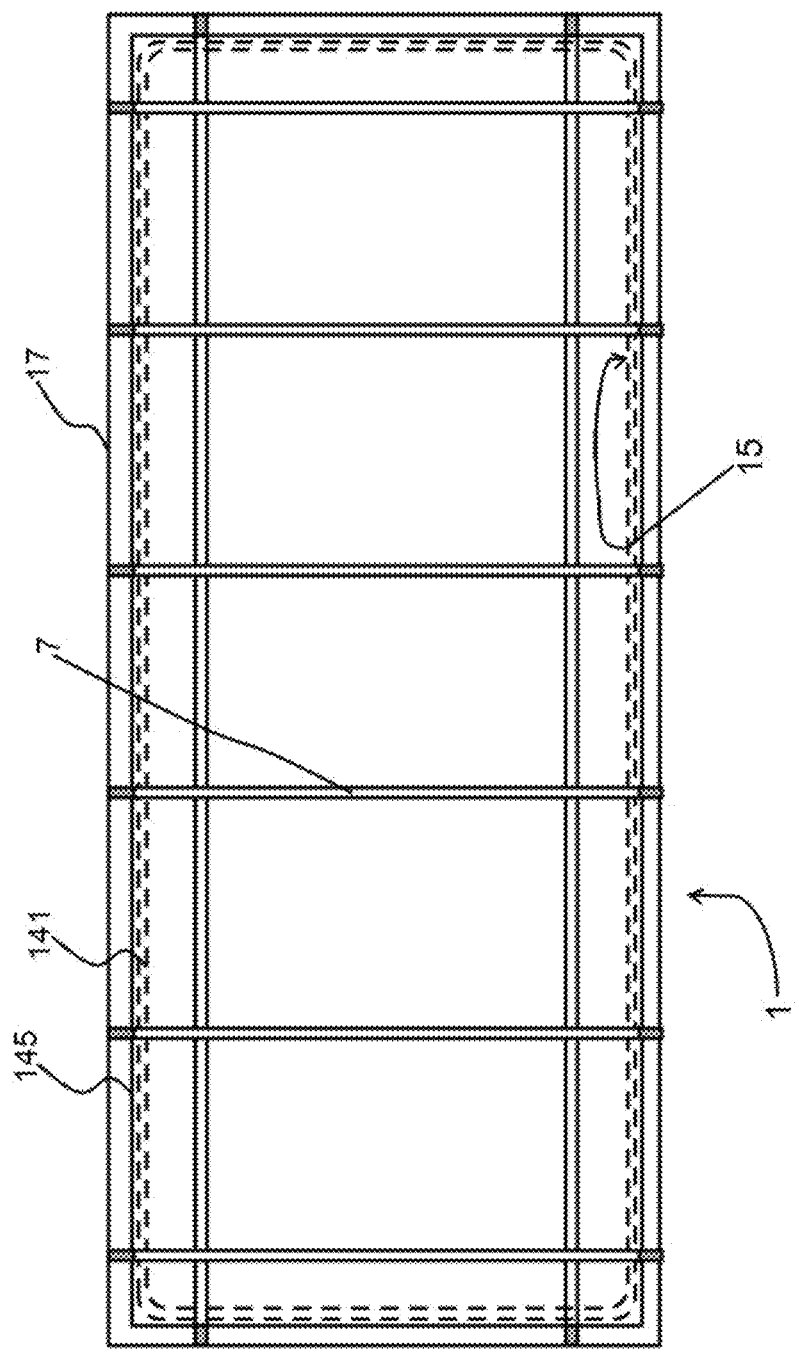
FIG. 2 is the schematic cross section of the main body of inpatient unit in another embodiment of the present invention.
Figure 3:
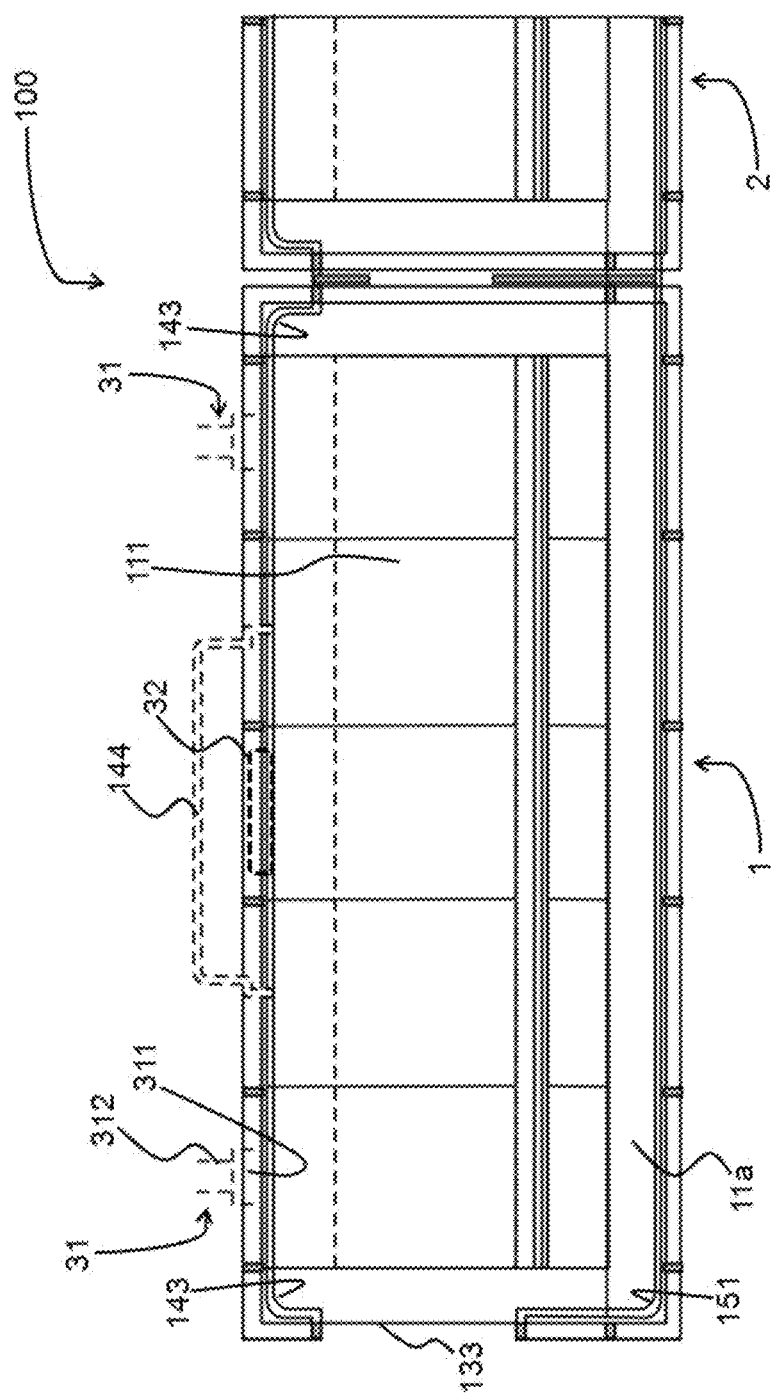
FIG. 3 is the schematic cross section of an easily assembled prefabricated modular inpatient unit in one embodiment of the present invention.
Figure 4:
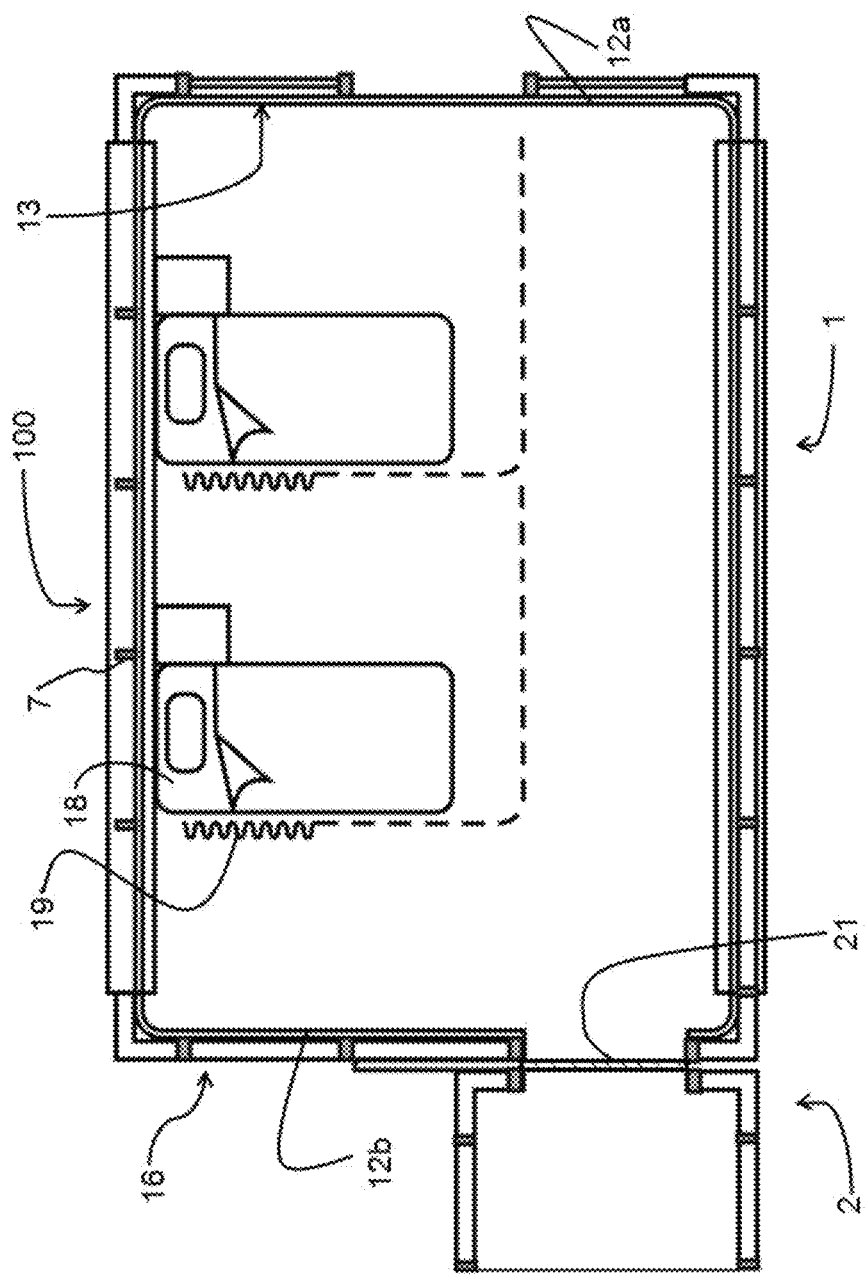
FIG. 4 is the top sectional view of the easily assembled prefabricated modular inpatient unit in another embodiment of the present invention.
Figure 5:
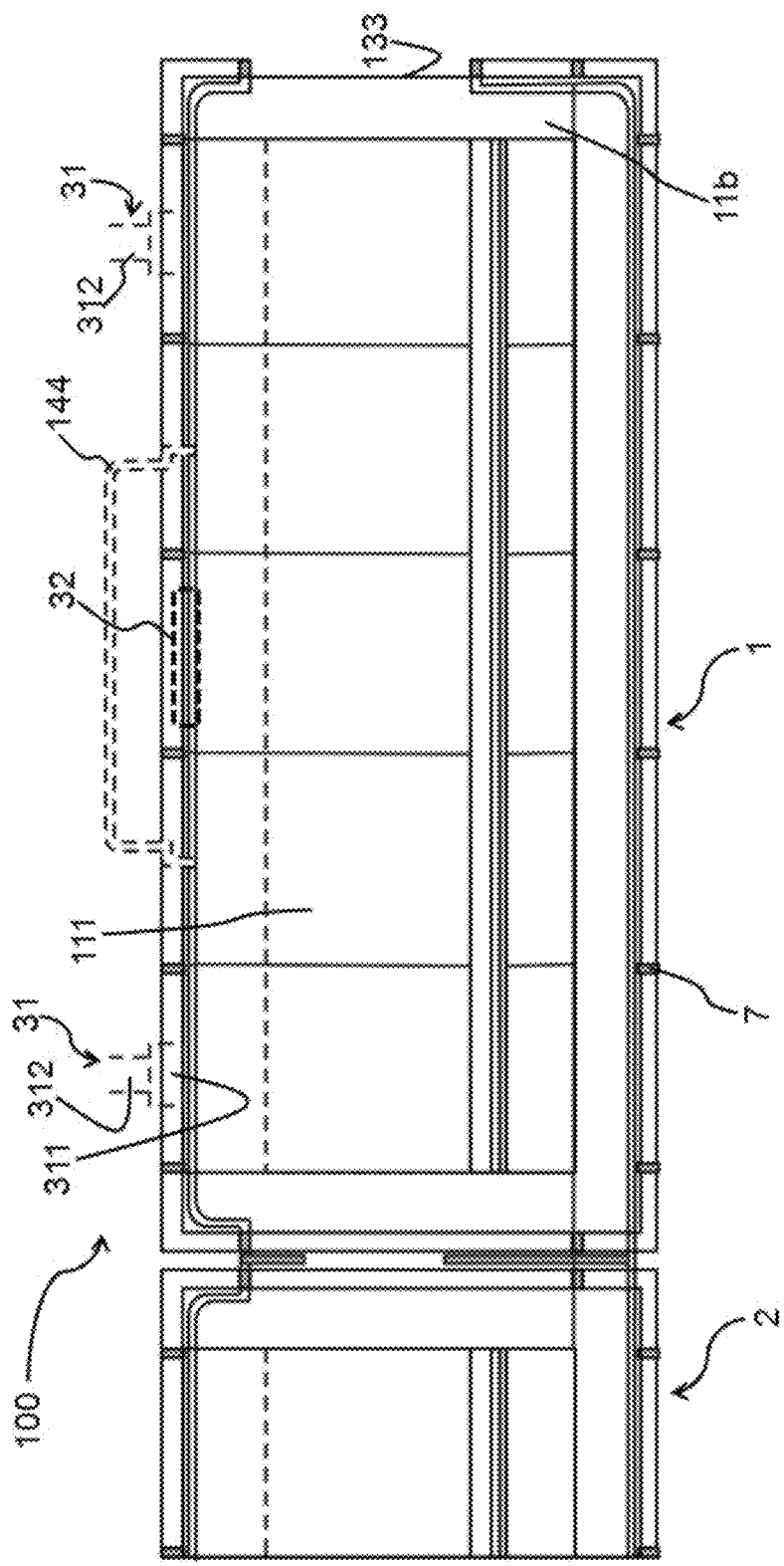
FIG. 5 is the schematic cross section of the easily assembled prefabricated modular inpatient unit in another embodiment of the present invention.
Figure 6:
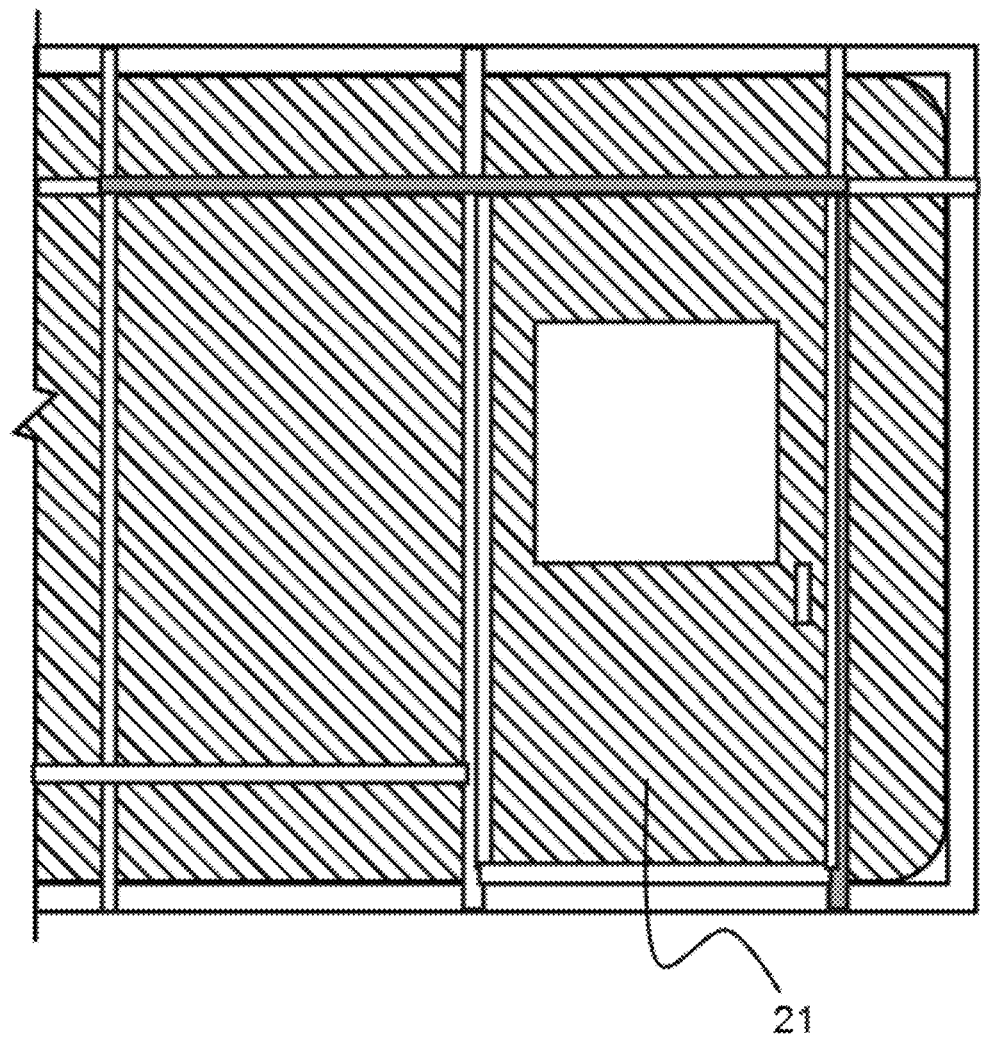
FIG. 6 is the schematic diagram of an inner partition door in one embodiment of the present invention.
Figure 7:
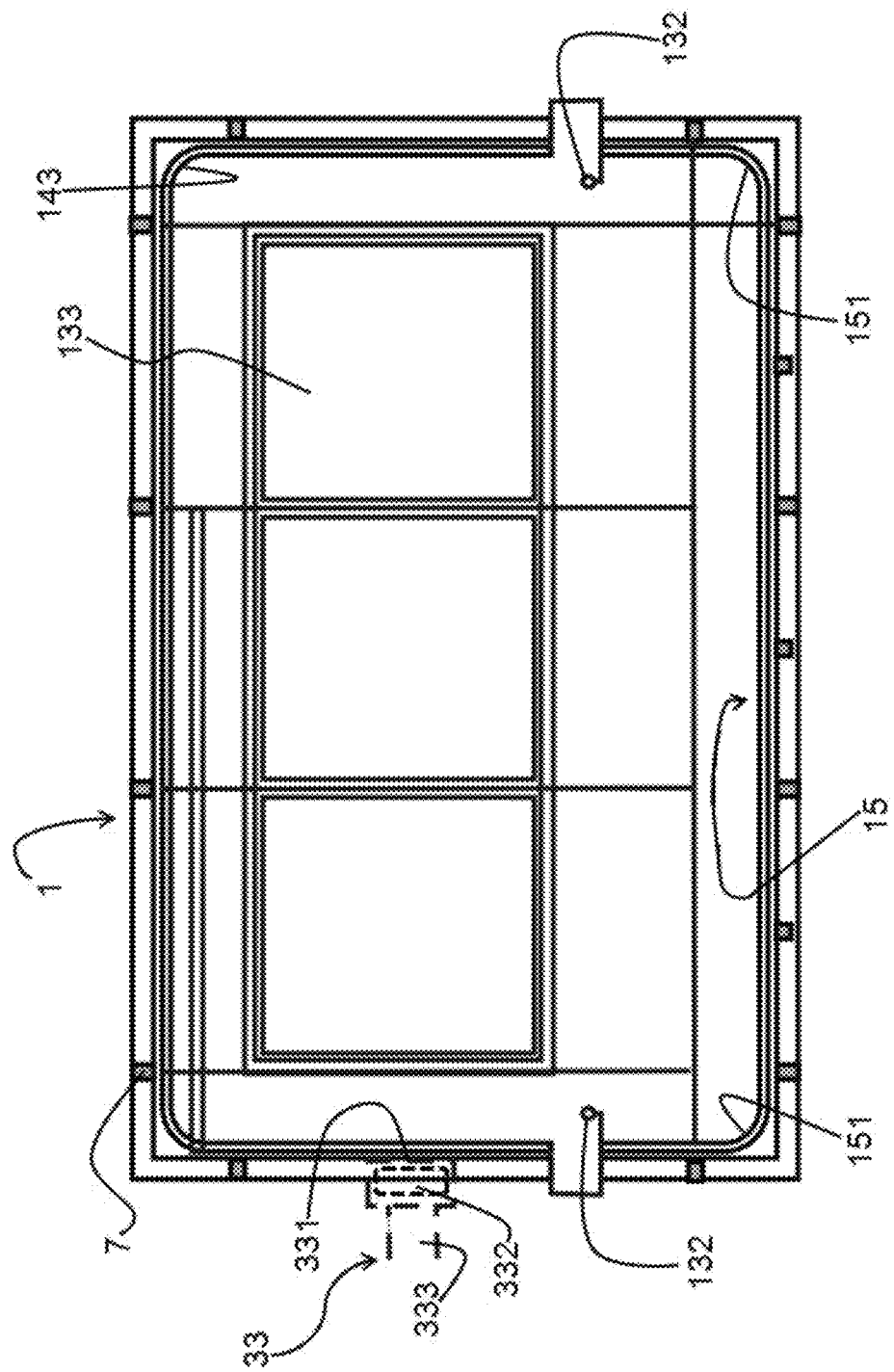
FIG. 7 is the schematic cross section of the main body of inpatient unit in the other embodiment of the present invention.
Figure 8:
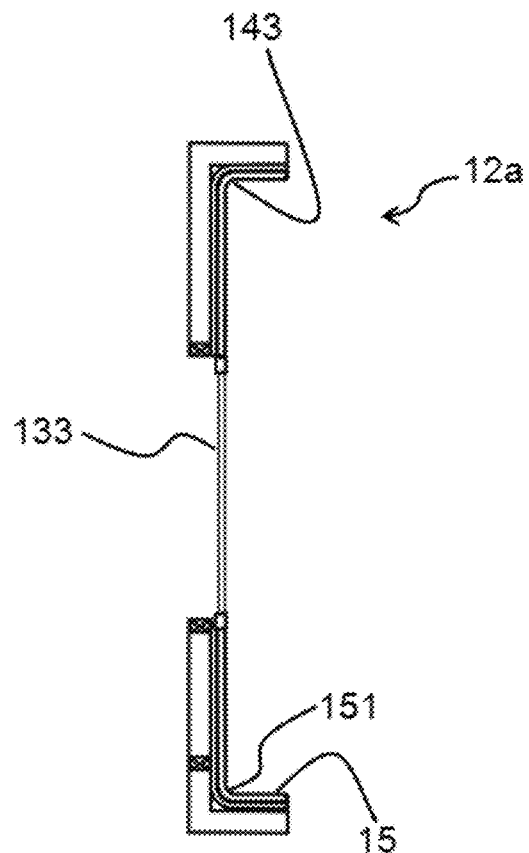
FIG. 8 is the schematic diagram of a transparent window in one embodiment of the present invention.
Figure 9:
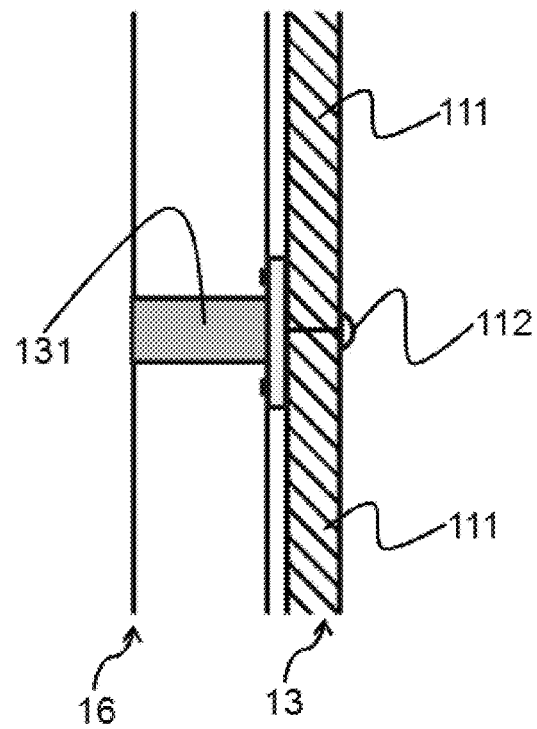
FIG. 9 is the schematic diagram of an inner wall in one embodiment of the present invention.

The technical content of the present invention is described below by specific implementation patterns, those who are familiar with this craft can understand the advantages and effects of the present invention according to the content disclosed in this specification. However, the present invention can be practiced or applied in different forms of patterns without deviating from the characteristics or spirit of the present invention.

An embodiment of the present invention in the description is used for description, representing a specific function, structure or feature involved in the present invention. The term "an embodiment" in the description is not always the same embodiment, or a specific or substitute embodiment mutually exclusive of other embodiments. In other words, some embodiments can describe some specific features, whereas other embodiments don't. In addition, the well-known structures, elements or connections of related fields are not described in detail, so as to avoid obscuring the particular features of the present invention.

Please refer to FIG. 1-14 for an easily assembled prefabricated modular inpatient unit 100 which allows continuous reconfiguration and redeployment, comprising a main body of inpatient unit 1. The main body of inpatient unit 1 at least includes two long walls 11a, 11b, two short walls 12a, 12b, a ceiling 14, a PVC seamless floor 15 (as shown in FIG. 1, FIG. 3-5, FIG. 7). The two long walls 11a, 11b and two short walls 12a, 12b are arranged oppositely on both sides of the main body of inpatient unit 1 respectively. The two sides of the two short walls 12a, 12b are connected to the long walls 11a, 11b respectively and arranged oppositely on the other two sides. The long walls 11a, 11b and the short walls 12a, 12b are interconnected to form an inner wall 13 and an outer wall 16 of the main body of inpatient unit 1. The ceiling 14 comprises an inner ceiling 141 and an outer ceiling 145. The inner wall 13 is directly connected to the inner ceiling 141 via extends upwards from the main body of inpatient unit 1. The outer wall 16 is directly connected to the outer ceiling 145 via extends upwards from the main body of inpatient unit 1.

Further, the long walls 11a, 11b and the short walls 12a, 12b are assembled of a plurality of inner unit panels 111 and a plurality of outer unit panels. The plurality of outer unit panels assemble the outer wall. The adjacent inner unit panels 111 are fixed by a plurality of panel connecting pieces 112. In other words, the main body of inpatient unit 1 of the present invention can be assembled quickly by the modular design of the inner unit panels 111 and panel connecting pieces 112. In addition, the joints of adjacent inner unit panels 111 towards the inner space of modular inpatient unit are tightened by a plurality of antibacterial airtight pieces. The antibacterial airtight pieces are made of a polyolefins thermoplastic vulcanizate (TPV). The antibacterial airtight piece can abut on the panel connecting piece 112 in an embodiment, so as to prevent the indoor air from leaking out of the main body of inpatient unit. The inner unit panels 111 are made of recycled polyethylene terephthalate (PET). Moreover, the surface of the inner unit panels 111 is spray coated with aluminum nano-photocatalyst material.

Figure 10:
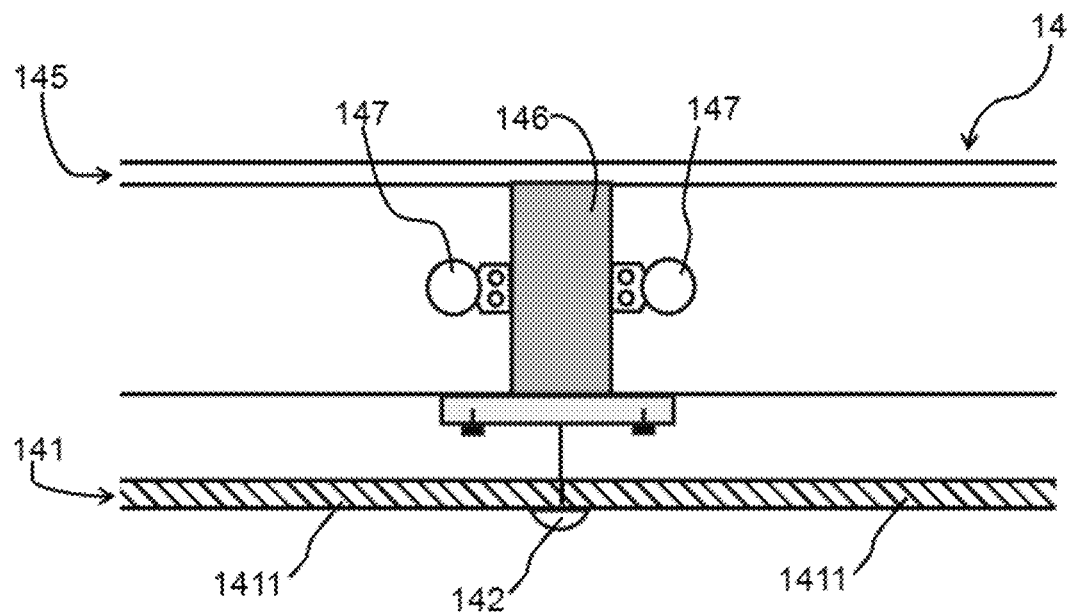
FIG. 10 is the schematic diagram of a ceiling in one embodiment of the present invention.
Figure 11:
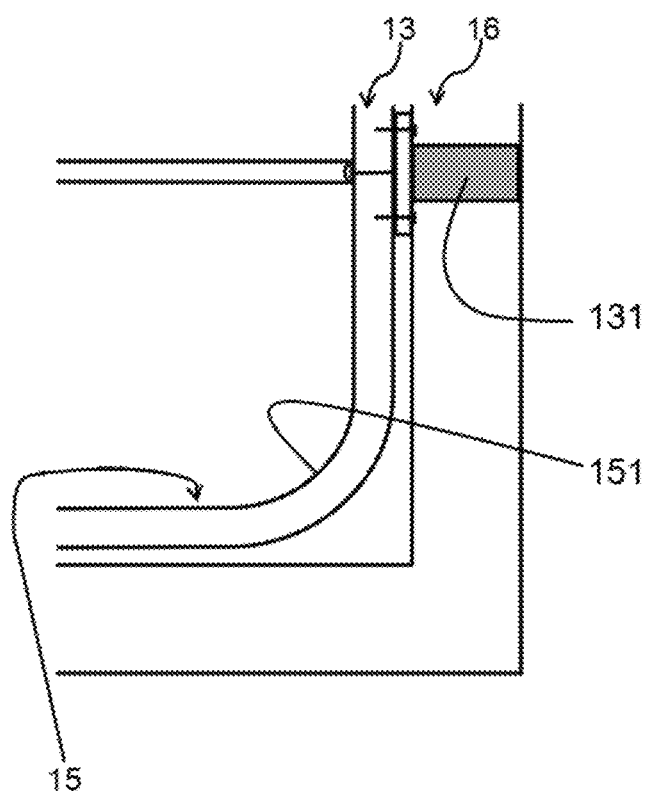
FIG. 11 is the schematic diagram of the inner wall connected to a PVC seamless floor.
Figure 12:
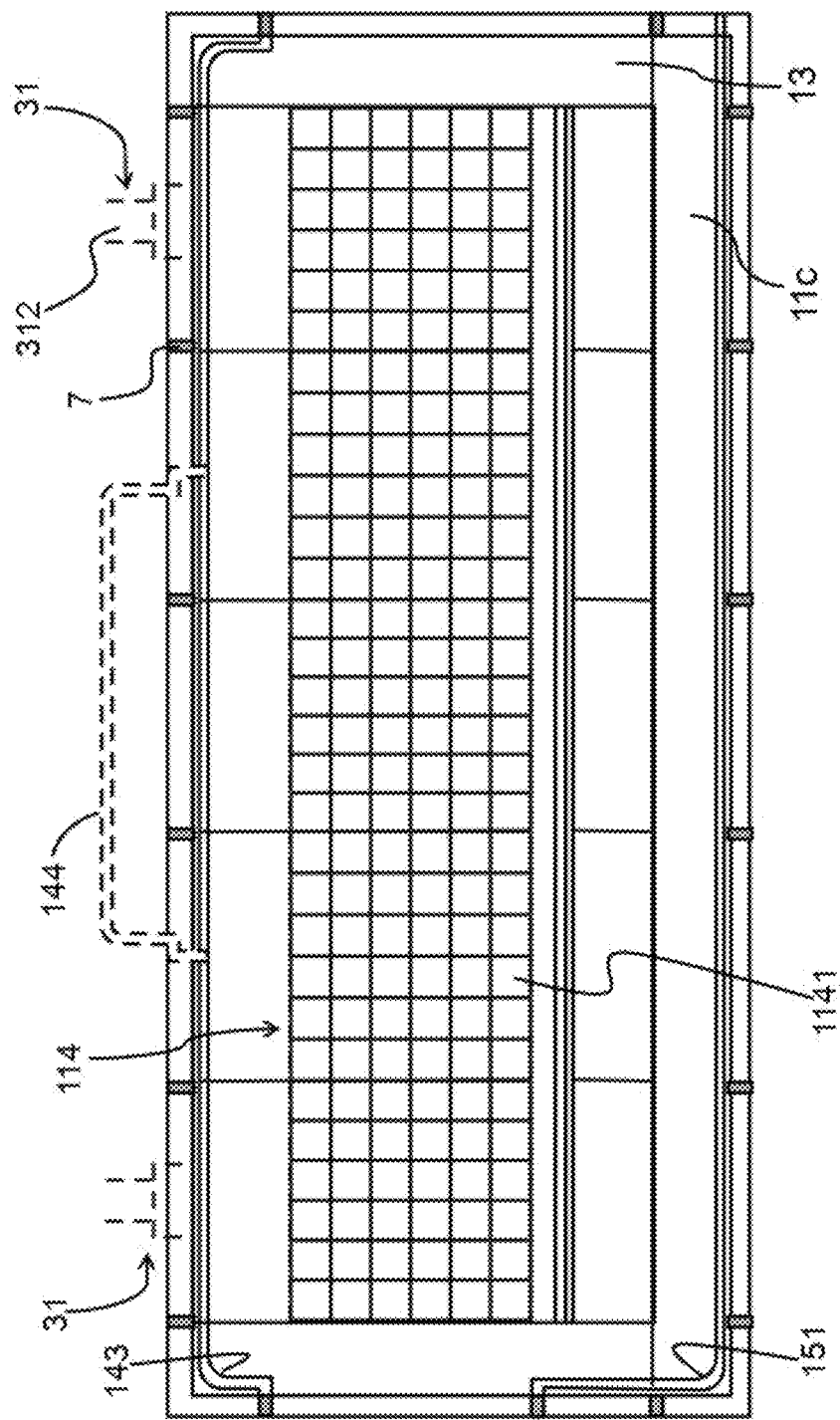
FIG. 12 is the schematic diagram of acoustic panels in one embodiment of the present invention.
Figure 13:
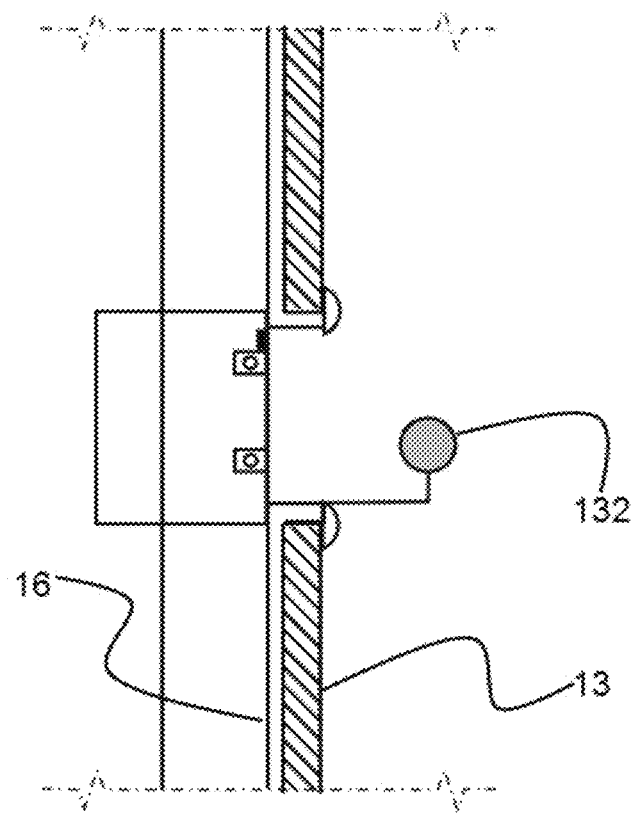
FIG. 13 is the schematic diagram of handrails in one embodiment of the present invention.
Figure 14:
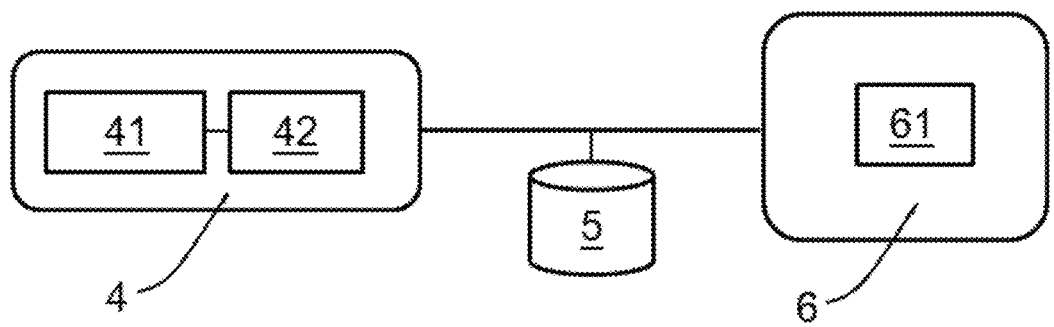
FIG. 14 is the schematic diagram of a vital signs real-time monitoring system, an Intelligent Internet of Things System and an artificial intelligence calculation module in an embodiment of the present invention.

On the other side, the joint of inner ceiling 141 and inner wall 13 towards the inner space of modular inpatient unit forms a top circular arc chamfer 143. The inner ceiling 141 towards the inner space of modular inpatient unit is assembled of a plurality of polycarbonate recycled plastic hollow panels 1411 (as shown in FIG. 10). The structure of the polycarbonate recycled plastic hollow panel 1411 comprises superposed hollow rectangular tube columns made by recycled plastic. Additionally, the adjacent polycarbonate recycled plastic hollow panels 1411 are fixed by a plurality of top panel connecting pieces 142. The ceiling 14 is provided with at least one UV-lamp. Therefore, it could kill 99% of bacteria and viruses via the surface of inner wall made by PET spray coated with aluminum nano-photocatalyst material and the UV-lamp.

Further, a strut 146 is arranged between inner ceiling 141 and outer ceiling 145. The strut 146 enables the inner ceiling 141 to support the outer ceiling 145. The strut 146 is provided with a LED illuminator 147. The LED illuminator 147 provides lighting for medical care personnel and patients in the room.

Moreover, the PVC seamless floor 15 is opposite to the inner ceiling 14 and arranged under the inner wall 13. The PVC seamless floor 15 is formed by laying a PVC sheet. The joint of the PVC seamless floor 15 and one of the long walls or the short walls towards the inner space of the modular inpatient unit forms a seamless bottom circular arc chamfer 151. In other words, it could be achieved to reduce the risk of cross infection and prevent the indoor air from leaking out of the main body of inpatient unit with the PVC seamless floor 15, the seamless bottom circular arc chamfer 151, the antibacterial airtight piece, the inner unit panels 111, and the top circular arc chamfer.

Further, the inner unit panels 111, polycarbonate recycled plastic hollow panels 1411 and antibacterial airtight pieces provided by the present invention are characterized by a few seams, tight bonding and good thermal insulation, preventing abnormal leak and reducing the air conditioning cost. In addition, the inner unit panels 111, polycarbonate recycled plastic hollow panels 1411 and antibacterial airtight pieces provided by the present invention are characterized by wear resistance, acid resistance, alkali resistance and UV resistance, preventing material deterioration and abnormal leak.

The present invention is not limited to this, in another embodiment, the prefabricated modular inpatient unit of the present invention includes a cover member 17. The cover member 17 covers the modular inpatient unit. On the one hand, it enables the present invention to resist dust more effectively. On the other hand, it can be the structure for temporary erection of electrical equipments. Moreover, a horizontal beam 131 is arranged between inner wall 13 and outer wall 16. The horizontal beam 131 and strut 146 further reinforce the overall structure of the prefabricated modular inpatient unit. The inner wall, outer wall, inner ceiling and outer ceiling are not limited to single-layer structure in the present invention. Additionally, the outer wall 16 opposite to the top circular arc chamfer 143 and seamless bottom circular arc chamfer 151 can be a circular arc chamfer in an embodiment, or can be a right angle in another embodiment.

Further, the present invention is also provided with a negative pressure air conditioning system in another embodiment. The negative pressure air conditioning system includes a fresh air supply unit 31, an independent air conditioning cold setting unit 32 and an air return unit 33. The independent air conditioning cold setting unit 32 is arranged at the ceiling 14. The fresh air supply unit 31 has at least one fresh air outlet 311 in the ceiling 14 through an air supply pipe 312. The fresh air supply unit supplies fresh air inside the main body of inpatient unit. Additionally, a return air inlet 331 provided with one of the long walls at least is adjacent to one sickbed. The return air inlet 331 is connect to exhaust pipe 333.

The return air inlet 331 is provided with a high efficiency particulate air filter (HEPA) 332. The air return unit 33 can effectively pump the stale air out of the main body of inpatient unit, and the HEPA which can filter more than 99.97% of aerosol particles above 0.3 μm filters such harmful substances as viruses and pathogenic bacteria, controlling the spatial limit of effective exhaust and maintaining indoor negative pressure.

The negative pressure air conditioning system can effectively maintain negative pressure inside the main body of inpatient unit 1, so that the indoor air pressure is always lower than the outdoor air pressure, compelling the outdoor air to irreversibly flow into the indoor space through different structural joints, leading to unidirectional isolation of indoor air. Which is to say, when the patient coughs or sneezes, there are droplets containing pathogens generated, and the droplets in the air are likely to dehydrate to form dry particle cores or outside dry and inside wet particles, the residual infective power of particles may threaten the hospital staffs health. Therefore, the negative pressure air conditioning system can effectively control the contamination range of the biological aerosol derived from the patients, reducing the load of respiratory protections on the medical care personnel, and reducing the infection probability of medical care personnel resulted from inhaling biological aerosol (including droplets).

Further, the return air inlet is located in the wall near the sickbed 18. The fresh air outlet 311 is located in the ceiling. The fresh air supplied from the fresh air outlet 311 flows towards the sickbed, so that the harmful biological aerosol exhaled from the patient is unlikely to diffuse, and can flow into the return air inlet 331 nearby. Which is to say, the present invention continuously blow the fresh air into the main body of inpatient unit 1 through the fresh air outlet 311, and extracts the indoor contaminated air through the return air inlet 331, so that the concentration of noxious substances in the indoor air is reduced, and the effect of general ventilation is achieved.

On the other hand, the present invention is not limited to this, in another embodiment, a square steel tube 7 is vertically or laterally arranged outside the outer wall 16 of the main body of inpatient unit 1. In other words, the number of square steel tube 7 is at least 1. Which is to say, the number of square steel tubes may be 1, 2, 3, 4, 5, 6, 7, 8, 9 or more. Additionally, at least one square steel tube 7 can be vertically or laterally arranged at the top of the main body of inpatient unit 1, and at least one square steel tube 7 can be vertically or laterally arranged at the bottom of the main body of inpatient unit 1. Furthermore, in another embodiment of the present invention, the square steel tube 7 is inserted in the outer wall and/or outer ceiling. The main body of inpatient unit 1 is further stabilized by the square steel tubes, especially when the main body of inpatient unit 1 is located in a field outside the building, the effect of the aforementioned square steel tube is more significant.

Further, in the third embodiment of the present invention, one of the long walls 11 towards the inner space of the main body of inpatient unit 1 is provided with a plurality of acoustic panels 114. The acoustic panel 114 is assembled of a plurality of sound insulation platelets 1141, the external noise is reduced effectively, so that the patient in the main body of inpatient unit 1 can take an effective rest without noise disturbance. A sprinkler fire-extinguishing system 144 is arranged at the ceiling 14, it can spray water in time if a fire alarm occurs in the main body of inpatient unit 1.

In the fourth embodiment of the present invention, one of the short walls is provided with a transparent window 133 for medical care personnel to observe the patient in the room from the outside, or for the patient in the room to observe the outside. The transparent window 133 is arranged in the short wall with a metal frame. On the other hand, the inner wall is provided with a handrail 132 for supporting the patient walking indoors. In addition, the modular inpatient unit contains at least one sickbed 18 for the patient to rest, and a partition curtain 19 is arranged by the sickbed to protect the inpatient against disturbance or to provide partial privacy protection.

In the fifth embodiment of the present invention, it is further complied a negative pressure buffer anteroom 2. The negative pressure buffer anteroom 2 is connected by an inner partition door 21 slidably arranged between the negative pressure buffer anteroom 2 and the main body of inpatient unit 1. The negative pressure buffer anteroom 2 is provided with an outer partition door for communicating with and isolating the outside. Certainly, the present invention is not limited to this, the negative pressure buffer anteroom is provided with an independent negative pressure system and a suction opening, it can be the air pressure buffer space for preventing the negative pressure failure of the main body of inpatient unit 1, and the medical care personnel can get changed and sanitized herein before entering and after leaving the main body of inpatient unit, so as to effectively reduce the infection risk of medical care personnel. In addition, the negative pressure buffer anteroom 2 can be reinforced by a square steel tube 7 as the main body of inpatient unit 1.

In the sixth embodiment of the present invention, it is further complied a vital signs real-time monitoring system 4. The vital signs real-time monitoring system at least includes a dynamic sensor camera 41 and a dynamic video camera 42 arranged at the ceiling.

In the seventh embodiment of the present invention, it is further complied an Intelligent Internet of Things System 5. The Intelligent Internet of Things System 5 communicated with the vital signs real-time monitoring system 4 and an artificial intelligence calculation module 6.

In other words, the medical care personnel can thoroughly observe the patient's vital signs and related instruments and values, such as pulse rate, temperature, respiratory rate, blood pressure, oxygen saturation, electrocardiography, consciousness, ventilator and infusion pump monitoring through a remote real-time monitoring device 61 outside the main body of inpatient unit with the vital signs real-time monitoring system 4, the Intelligent Internet of Things System 5 and the artificial intelligence calculation module 6, so as to avoid cross infection of medical care personnel and patient. Added to this, if the patient's physiological condition deviates from the normal range of values, the vital signs real-time monitoring system 4, Intelligent Internet of Things System 5 and artificial intelligence calculation module 6 will give an emergency signal through the remote real-time monitoring device 61 after calculation, so as to remind the medical care personnel.

In other words, the present invention is an easily assembled prefabricated modular inpatient unit which allows continuous reconfiguration and redeployment, the peripheral walls (outer walls and inner walls), top (ceiling) and bottom (floor) are assembled by such fasteners as panel connecting pieces to form a modular inpatient unit. The prefabricated modular inpatient unit of the present invention can be used to assemble different kinds of wards quickly in any place, e.g. intensive care unit, general ward, isolation room or negative pressure ward. It can be used as general ward in outdoor environment, e.g. parking lot, stadium and gymnasium, and it is convertible according to application requirement. Furthermore, the aforementioned prefabricated modular panels and related parts and components of the present invention have small sizes, convenient for transportation in aeroplanes, vehicles and elevators with limited inner space, and they can be assembled in a short period of time, for example, but not limited to 1 hour, 2 hours, 6 hours, 12 hours, 24 hours, 36 hours or 48 hours, and the general ward can be converted into a room with isolation, negative pressure and ICU functions in a short period of time according to service behavior.

Considering the patient's physical and mental health, a design with visual aestheticism is added in the modular inpatient unit. For example, the acoustic panel 114 can be designed as a gradient wall with a healing image, the wall design can be used as an artistic wall painting, and can absorb noise, so as to help the patient relieve emotion and reduce mental pressure.

To sum up, the prefabricated modular inpatient unit of the present invention has the following advantages: (1) not limited to site: the present invention can change freely according to occasion and space, it can be assembled in buildings, health centers, stadiums and parking lots, breaking prior limitations; (2) not limited to transportation method: the prefabricated modular panels and related parts and components disclosed in the present invention have small sizes, they can be transported by various transporters with limited inner space; (3) medical care personnel don't need to stay with the patient all the time: the medical care personnel can monitor the patient's real-time physiological condition through the remote real-time monitoring device with the vital signs real-time monitoring system, Intelligent Internet of Things System and artificial intelligence calculation module, the infection risk of medical care personnel can be reduced effectively; the prefabricated modular inpatient unit of the present invention provides an independent ventilation system and a negative pressure buffer anteroom for the medical care personnel to get sanitized and changed; (4) not limited to the existing knowledge and technology: the prefabricated modular inpatient unit of the present invention can be used as a conventional ward at ordinary times, and can be converted into a negative pressure ward quickly in epidemic period. It can be reconverted into a general ward after epidemic.

Although the invention has been explained in relation to its preferred embodiment, it is to be understood that many other possible modifications and variations can be made without departing from the spirit and scope of the invention as hereinafter claimed.

The invention claimed is:

1. A convertibly prefabricated modular inpatient unit with enabling continuous reconfiguration and redeployment, comprising a main body of the inpatient unit, the main body of the inpatient unit comprises two first walls and two second walls,
wherein each second wall extends outward from one side of each first wall in a direction perpendicular to each first wall, wherein one of the first walls is parallel to another of the first walls, and one of the second walls is parallel to another of the second walls, the two first walls and the two second walls are interconnected to form an inner wall and an outer wall of the main body of the inpatient unit;

wherein the two first walls and the two second walls are assembled of a plurality of inner unit panels and a plurality of outer unit panels, the plurality of outer unit panels assemble the outer wall, the plurality of inner unit panels are arranged at intervals and adjacent inner unit panels are fixed connected by a plurality of panel connecting pieces, the plurality of inner unit panels are spray coated with an aluminum nano-photocatalyst material, and adjacent inner unit panels are connected by a plurality of antibacterial airtight pieces towards an inner space of the inpatient unit;

an inner ceiling, wherein the inner ceiling connects with the inner wall towards the inner space of the inpatient unit to form a top circular arc chamfer;

a PVC seamless floor that is arranged opposite the inner ceiling under the inner wall, the PVC seamless floor is formed by laying a PVC sheet, wherein the PVC seamless floor connects with one of the first walls or the second walls towards the inner space of the inpatient unit to form a seamless bottom circular arc chamfer; and wherein the inner ceiling is provided with at least one fresh air outlet and an independent air conditioning cold setting unit, wherein one of the first walls is provided with a return air inlet and is adjacent to one sickbed, wherein the return air inlet is provided with a HEPA for treatment of exhaust air, wherein the at least one fresh air outlet, the return air inlet and the independent air conditioning cold setting unit assemble a negative pressure air conditioning system.

2. The convertibly prefabricated modular inpatient unit with enabling continuous reconfiguration and redeployment of claim 1, further comprising a negative pressure buffer anteroom that is connected by an inner partition door slidably arranged between the negative pressure buffer anteroom and the main body of the inpatient unit.

3. The convertibly prefabricated modular inpatient unit with enabling continuous reconfiguration and redeployment of claim 1, further comprising a plurality of square steel tubes, wherein the plurality of square steel tubes are vertically or laterally arranged outside the outer wall of the main body of the inpatient unit, the plurality of square steel tubes are vertically or laterally arranged against a top and bottom of the main body of the inpatient unit.

4. The convertibly prefabricated modular inpatient unit with enabling continuous reconfiguration and redeployment of claim 1, further comprising a vital signs real-time monitoring system, wherein the vital signs real-time monitoring system comprises a dynamic sensor camera and a dynamic video camera arranged at the inner ceiling.

5. The convertibly prefabricated modular inpatient unit with enabling continuous reconfiguration and redeployment of claim 4, further comprising an Intelligent Internet of Things System, wherein the Intelligent Internet of Things System communicates with the vital signs real-time monitoring system and an artificial intelligence calculation module respectively.

6. The convertibly prefabricated modular inpatient unit with enabling continuous reconfiguration and redeployment of claim 1, further comprising a UV-lamp, wherein the UV-lamp is arranged at the inner ceiling.

7. The convertibly prefabricated modular inpatient unit with enabling continuous reconfiguration and redeployment of claim 1, wherein the plurality of inner unit panels are provided with a plurality of acoustic panels on one of the first walls.

* * * * *